(12) United States Patent
Kuprathipanja

(10) Patent No.: US 6,252,127 B1
(45) Date of Patent: Jun. 26, 2001

(54) PROCESS FOR MONOMETHYL ACYCLIC HYDROCARBON ADSORPTIVE SEPARATION

(75) Inventor: Santi Kuprathipanja, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/222,423

(22) Filed: Dec. 29, 1998

(51) Int. Cl.⁷ .................................. C07C 7/12; C07C 7/13
(52) U.S. Cl. ..................... 585/826; 585/820; 208/310 R; 208/310 Z
(58) Field of Search .................... 585/820, 826; 208/310 R, 310 Z

(56) References Cited

U.S. PATENT DOCUMENTS

| | | | |
|---|---|---|---|
| 2,477,382 | | 7/1949 | Lewis .................... 260/671 |
| 4,329,280 | * | 5/1982 | Cleary et al. .............. 530/207 |
| 4,367,364 | | 1/1983 | Kulprathipanja et al. ...... 585/826 |
| 4,455,444 | | 6/1984 | Kulprathipanja et al. ...... 585/826 |
| 4,455,445 | * | 6/1984 | Neuzil et al. ............. 585/820 |
| 4,956,621 | | 9/1990 | Volles ................... 585/826 |
| 4,982,052 | * | 1/1991 | Nolte .................... 585/822 |
| 5,055,633 | * | 10/1991 | Volles ................... 585/826 |
| 5,055,634 | * | 10/1991 | Volles ................... 585/826 |
| 5,220,102 | * | 6/1993 | Funk et al. ............... 585/829 |
| 5,262,144 | | 11/1993 | McCulloch ................ 423/328.2 |
| 5,276,246 | | 1/1994 | McCulloch et al. .......... 585/829 |
| 5,292,990 | | 3/1994 | Kantner et al. ............ 585/820 |

FOREIGN PATENT DOCUMENTS

99/07656   2/1999   (WO) .

OTHER PUBLICATIONS

Vora, B.V., P.R. Pujado, J.B. Spinner, "Latest LAB Developments," *Hydrocarbon Processing*, Nov. 1984, p. 86–90.

Schulz, R.C., P.R. Pujado, B.V. Vora, "LAB Production," Poster Session at the 2nd World Conference on Detergents, Montreux, Switzerland, Oct. 5–10, 1986.

Hoering, Thomas C. and David H. Freeman, "Shape-Selective Sorption of Monomethylalkanes by Silicate, a Zeolite Form of Silica," *Journal of Chromatography*, 316(1984), p. 333–341.

* cited by examiner

*Primary Examiner*—Walter D. Griffin
(74) *Attorney, Agent, or Firm*—John G. Tolomei; John F. Spears, Jr.

(57) ABSTRACT

Monomethyl branched $C_{10}$–$C_{15}$ paraffins or olefins are recovered from a mixture comprising other nonnormal hydrocarbons such as di-isoparaffins, di-isoolefins and aromatics by adsorptive separation in a process which uses an adsorbent comprising silicalite and a desorbent comprising a $C_5$ or $C_6$ cycloparaffin. The recovered monomethyl hydrocarbons may then be used to form a monomethyl branched alkylaromatic hydrocarbon useful as a detergent precursor.

7 Claims, No Drawings

PROCESS FOR MONOMETHYL ACYCLIC HYDROCARBON ADSORPTIVE SEPARATION

FIELD OF THE INVENTION

The subject invention relates to a process for the adsorptive separation of hydrocarbons. More specifically, the invention relates to a process for the continuous simulated countercurrent adsorptive separation of monomethyl paraffins or olefins from a mixture of these and other hydrocarbons. A preferred application of the process is the separation of $C_{10}$–$C_{15}$ monomethyl paraffins from a kerosene boiling range fraction.

BACKGROUND OF THE INVENTION

Most of the detergents in use today are derived from precursor petrochemicals. One of the currently predominant precursors is linear alkyl benzene (LAB), which is commonly produced by the alkylation of benzene with a long chain linear olefin. The subject invention is directed to the production of monomethyl acyclic olefins and paraffins, which may be recovered as a product in their own right, or used in the production of various petrochemicals as through alkylation or oxygenation. The following discussion will mainly address the use of the recovered hydrocarbons in the production of detergent precursor petrochemicals.

Several quality characteristics of alkylbenzenesulfonate (ABS) detergents are set by the chemical structure of the alkyl side chain. For instance, linear alkyl groups have the advantage of increased biodegradability. Other characteristics of the detergent such as its effectiveness in hard water and its foaming tendency are also influenced by the structure of the side chain and its constituents. It has now been determined that highly desirable detergent precursors can be formed from olefins which contain a single methyl side chain on the main alkane chain. The subject invention is specifically directed to the production of monomethyl hydrocarbons for use in the production of these detergent precursors.

BACKGROUND ART

The large utility of detergents and other cleaners has led to extensive development in the areas of detergent production and formulation. While detergents can be formulated from a wide variety of different compounds much of the world's supply is formulated from chemicals derived from linear alkyl benzenes. The compounds are produced in petrochemical complexes in which an aromatic hydrocarbon, typically benzene, is alkylated with an olefin of the desired structure and carbon number. Typically the olefin is actually a homologous series of different olefins having a range of three to five carbon numbers. The olefin(s) can be derived from several sources. For instance, it can be derived from the oligomerization of $C_3$ or $C_4$ olefins or from the polymerization of ethylene. Economics has led to the production of olefins by the dehydrogenation of the corresponding paraffin being the preferred route to produce the olefin. Paraffins having 10 to 15 carbon atoms per molecule are found in the kerosene boiling range fraction of crude oils or processed fractions of crude oil, and therefore recovery of the desired paraffins from kerosene has become the leading commercial source of the olefinic precursors. The production of the olefins starts with the recovery of paraffins of the same carbon number by adsorptive separation from kerosene. The paraffins are then passed through a catalytic dehydrogenation zone wherein some of the paraffins are converted to olefins. The resultant mixture of paraffins and olefins is then passed into an alkylation zone in which the olefins are reacted with the aromatic substrate. This overall flow is shown in U.S. Pat. No. 2,477,382 issued to A. H. Lewis. A more complete description of this integrated process employing paraffin dehydrogenation and alkylation is shown in an article at page 86 of the November, 1984 edition of *Hydrocarbon Processing*.

A description of the process and of the use of simulated moving bed adsorptive separation to recover the paraffins from the kerosene boiling range petroleum fraction is provided in a presentation made by R. C. Schulz et al. at the 2nd World Conference on Detergents in Montreux, Switzerland on Oct. 5–10, 1986. This shows several incidental steps in the process such as fractionation and hydrotreating. The subject invention differs from the process shown in this reference in that the paraffins recovered in the subject process are recovered from the stream labeled as the raffinate stream of the adsorptive separation unit, rather than the extract stream as shown in the reference. This is because the reference seeks to recover pure straight chain paraffins while the subject process is directed to the recovery of a branched chain paraffin. The raffinate stream of the reference can be charged into the subject process as the feed stream The success of a particular adsorptive separation is determined by many factors. Predominant in this are the composition of the adsorbent (stationary phase) and desorbent (mobile phase) employed in the process. The remaining factors are basically related to process conditions. The subject process employs an adsorbent comprising a molecular sieve referred to in the art as silicalite. The use of silicalite in the adsorptive separation of paraffins is described in U.S. Pat. No. 4,956,521 issued to W. K. Volles, which is directed to the production of higher octane gasoline blending components. The use of silicalite and zeolite 5A in the separation of monomethylalkanes is described in an article in the *Journal of Chromatography*, 316 (1984) 333–341. Silicalite has also been described as useful in separating normal paraffins from cyclic hydrocarbons and from branched chain hydrocarbons in U.S. Pat. Nos. 4,367,364 and 4,455,444 issued to S. Kulprathipanja and R. W. Neuzil. This separation differs from that performed in the subject process as it corresponds to that done in the previously cited article from the World Conference on Detergents, which is performed to recover normal paraffins.

The unique pore structure of silicalite has also led to efforts to employ it in the separation of linear (normal) olefins. Silicalite also has catalytic properties which can result in undesired conversion of olefins during this separation. The use of silicalite based adsorbents in the separation of linear olefins from nonlinear hydrocarbons and treatments of the silicalite to reduce its catalytic activity are described in U.S. Pat. Nos. 5,262,144 to McCulloch, 5,276,246 to McCulloch et al, and 5,292,990 to Kanter et al.

SUMMARY OF THE INVENTION

The invention is an adsorptive separation process for the recovery of monomethyl paraffins or olefins from admixture with other nonnormal paraffins or olefins, e.g., cyclic and multibranched paraffins. The process is characterized by the composition of the adsorbent and desorbent pair used in the process. The adsorbent used in the process is silicalite and the preferred desorbent is a cycloparaffin.

A broad embodiment of the invention may be characterized as a process for the adsorptive separation of a monomethyl acyclic hydrocarbon from a feed mixture comprising the monomethyl acyclic hydrocarbon and at least one other acyclic hydrocarbon, which process comprises contacting the feed mixture with a bed of an adsorbent comprising silicalite at adsorption promoting conditions and then removing a selectivley adsorbed monomethyl acyclic hydrocarbon from the adsorbent by contact with an desorbent compound comprising a $C_5$ or $C_6$ cycloparaffin. Preferably the desorbent also comprises a $C_5$ or $C_6$ normal paraffin.

DETAILED DESCRIPTION AND PREFERRED EMBODIMENTS

In numerous processes described in the patent literature molecular sieve adsorbents are used to separate various hydrocarbons and other chemical compounds such as aromatics, paraffins, chlorinated aromatics, and chiral compounds. The chemical compound separations which have been the specific focus of these processes include linear versus nonlinear aliphatic hydrocarbons and linear versus nonlinear olefinic hydrocarbons. Adsorptive separation is often used when (1) the compounds being separated have similar volatilities which prevents ready separation by fractional distillation or (2) a class separation covering a range of compounds is desired. The separation of $C_{10}$–$C_{14}$ linear paraffins from other $C_{10}$–$C_{14}$ hydrocarbons described in the references cited above is an example of such a class separation. Other examples of hydrocarbon separation by class is the recovery of either normal paraffins or aromatics from a feed mixture comprising both aromatics and mixed paraffins. The subject process is directed to the separation recovery of monomethyl paraffins from a mixture containing other non-normal paraffins. The feed stream to the subject process is preferably substantially free of normal (straight chain) paraffins and olefins of the same carbon number as the intended product. This preference is due to the tendency for normal paraffins and olefins to be preferentially adsorbed by silicalite.

The recovered monomethyl hydrocarbons have utility by themselves and can be used in the production of a variety of other chemicals, including oxygenates such as alcohols and ethers, and carbohydrates such as sugars. The recovered paraffins can therefore be subjected to conversion steps such as chlorination, nitration or alkylation, and result in the production of products such as solvents and lubricants. A preferred use of the monomethyl paraffins or olefins is in the production of detergent precursor compounds such as alkylbenzene. The alkylbenzene is then converted to a linear alkylsulfonate (LAS) by sulfonation. The product hydrocarbons can also be used in the production of other detergent precursors. Alkylbenzene compounds are consumed in the production of a variety of anionic surfactants compounded into detergents, cleaning compounds, bar soaps and laundry or dishwashing detergents. The monomethyl hydrocarbon or the monomethylalkylbenzene can be subjected to oxidation to form alcohols or acids or can be sulfonated.

The subject separation can be performed in a batch or continuous mode including the use of two or more adsorbent beds in cyclic operation. In this mode one or more beds is used for the separation while another bed is being regenerated. Significant operational and economic advantages accrue to performing the separation on a continuous basis which produces a product of uniform composition. The following description of the subject invention will therefore be presented basically in terms of the separation of various monomethyl paraffins from the other hydrocarbons as it would be performed in large scale simulated moving bed (SMB) units.

Most SMB adsorptive separation units simulate countercurrent movement of the adsorbent and the feed stream. This simulation is performed using established commercial technology wherein the adsorbent is held fixed in place as subbeds retained in one or more cylindrical adsorbent chambers. The positions at which the streams involved in the process enter and leave the chambers are slowly shifted along the length of the adsorbent chambers so that they enter or leave different subbeds. Normally there are at least four streams (feed, desorbent, extract and raffinate) employed in this procedure and the location at which the feed and desorbent streams enter the chamber and the extract and raffinate streams leave the chamber are simultaneously shifted in the same direction at set intervals. Each periodic incremental shift in the location of these transfer points delivers or removes liquid from a different subbed of adsorbent within the chamber. This shifting could be performed using a dedicated line for each stream at the entrance to each subbed. However, this will greatly increase the cost of the process and therefore the lines are reused. Only one line is normally employed for each subbed, and each bed line carries one of the four process streams at some point in the cycle.

These processes typically include at least three or four separate steps which are performed sequentially in separate zones within a mass of adsorbent retained in one or more vertical cylindrical adsorption chambers. Each of these zones normally is formed from a plurality of beds of adsorbent, sometimes referred to as subbeds, with the number of beds per zone ranging from 2 or 3 up to 8–10. The most widely practiced commercial process units typically contain about 24 beds. All of the beds are contained in one or more vertical vessels referred to herein collectively as the adsorbent chamber. The beds are structurally separated from one another by a horizontal liquid collection/distribution grid. Each grid is connected to a transfer line defining a transfer point at which process streams such as the raffinate and extract stream enter and leave the vertical adsorption chambers.

The general technique employed in the performance of a simulated moving bed adsorptive separation is well described in the open literature. For instance a general description of a process directed to the recovery of paraxylene by SMB was presented at page 70 of the September 1970 edition of *Chemical Engineering Progress* (Vol. 66, No 9). A generalized description of the process with an emphasis on mathematical modeling was given at the International Conference on "Fundamentals of Adsorption", Schloss Elmau, Upper Bavaria, Germany on May 6–11, 1983 by D. B. Broughton and S. A. Gembicki. Numerous other available references describe many of the mechanical parts of a simulated moving bed system, including rotary valves for distributing various liquid flows to the bed lines, the internals of the adsorbent chambers and control systems.

Countercurrent simulated moving bed systems are described in many available references, such as U.S. Pat. No. 2,985,589, incorporated herein by reference for its teaching of the practice of simulated moving bed adsorptive separation processes. Cyclic advancement of the input and output streams of this simulation can be accomplished by a manifolding system or by rotary disc valves as shown in U.S. Pat. Nos. 3,040,777 and 3,422,848. Equipment utilizing these principles can vary in size from the pilot plant scale shown in U.S. Pat. No. 3,706,812 to commercial petrochemical plant scale, with flow rates ranging from a few cc per hour to many thousands of gallons per hour.

Large scale plants normally employ rotary valves having a port for each transfer line while small scale and high pressure units tend to use valves having only two or three ports. The invention may also be practiced in a cocurrent continuous process, like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated herein, for additional description of these adsorption fundamentals.

During the adsorption step of the process a feed mixture containing a mixture of compounds is contacted with the adsorbent at adsorption conditions and one compound(s) or class of compounds is selectively adsorbed and retained by the adsorbent while the other compounds of the feed mixture are relatively unabsorbed. Normally the desired compound is adsorbed. The feed mixture may contain a large variety of compounds including isomers of the desired compound. For instance, a mixed xylene feed stream may contain ethylbenzene and/or C, aromatics and can be processed to recover a specific isomer by a suitable adsorbent/desorbent pair operated at suitable conditions. Differing sieve/desorbent combinations are used for different separations. For instance, X zeolites, specifically X zeolites exchanged with barium or barium and potassium ions at their exchangeable sites, are the preferred adsorbents for p-xylene recovery from xylene mixtures. When the adsorbent contains a near equilibrium loading of the more selectively adsorbed compound, it is referred to as a "rich" adsorbent. In the next step of the process, the unabsorbed (raffinate) components of the feed mixture are then removed from the interstitial void spaces between the particles of adsorbent and from the surface of the adsorbent. This depleted liquid and any desorbent which becomes admixed with it during passage through the adsorption zone in this step is removed from the process as a process stream referred to as the raffinate stream. The adsorbed compound is then recovered from the rich adsorbent by contacting the rich adsorbent with a stream comprising the desorbent material at desorption conditions in a desorption step. The desorbent displaces the desired compound to form an extract stream, which is normally transferred to a fractionation zone for recovery of the desired compound from the extract stream containing a mixture of the desired compound and desorbent. It should be noted that in some instances the desired product of the process can be in the raffinate stream rather than the extract stream and the process adsorbs undesired compounds.

For purposes of this invention, various terms used herein are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

At least portions of the extract stream and the raffinate stream are passed to separation means, typically fractional distillation columns, where at least a portion of desorbent material is recovered and an extract product and a raffinate product are produced. The terms "extract product" and "raffinate product" mean streams produced by the process containing, respectively, an extract component and a raffinate component in higher concentrations than those found in the extract stream and the raffinate stream withdrawn from adsorbent chamber. The extract stream may be rich in the desired compound or may only contain an increased concentration. The term "rich" is intended to indicate a concentration of the indicated compound or class of compounds greater than 50 mole percent.

It has become customary in the art to group the numerous beds in the adsorption chambers into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired isomer and accompanying desorbent are removed from the adsorbent in the form of the extract stream. Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorptive Separation section of the *Kirk-Othmer Encyclopedia of Chemical Technology* at page 563. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

It is an objective of the subject invention to provide an improved process for the simulated moving bed adsorptive separation of chemical compounds. It is a further objective to provide an improved process for the adsorptive separation of monomethyl hydrocarbons from other hydrocarbons. It is a specific objective to provide a simulated moving bed process to recover mixed monomethyl paraffins from a feed stream comprising a broad boiling mixture of branched paraffins and possibly other nonlinear hydrocarbons having a range of carbon numbers.

It has been found that these objectives can be achieved by employing a novel adsorbent-desorbent pair comprising an adsorbent comprising silicalite and a desorbent containing a linear paraffin and/or cycloparaffin. The preferred desorbent is a mixture of a $C_5$ to $C_8$ normal paraffin and a methylcycloparaffin.

The preferred adsorbent comprises silicalite. Silicalite is well described in the literature. It is disclosed and claimed in U.S. Pat. No. 4,061,724 issued to Grose et al. A more detailed description is found in the article, "Silicalite, A New Hydrophobic Crystalline Silica Molecular Sieve," *Nature*, Vol. 271, Feb. 9, 1978 which is incorporated herein by reference for its description and characterization of silicalite. Silicalite is a hydrophobic crystalline silica molecular sieve having intersecting bent-orthogonal channels formed with two cross-sectional geometries, 6Å circular and 5.1–5.7 Å elliptical on the major axis. This gives silicalite great selectivity as a size selective molecular sieve. Due to its aluminum free structure composed of silicon dioxide silicalite does not show ion-exchange behavior. Thus silicalite is not a zeolite.

The practice of the subject invention requires no significant variation in operating conditions, adsorbent or desorbent composition in the adsorbent chambers. That is the adsorbent preferably remains at the same temperature throughout the process.

The active component of the adsorbent is normally used in the form of particle agglomerates having high physical strength and attrition resistance. The agglomerates contain the active adsorptive material dispersed in an amorphous, inorganic matrix or binder, having channels and cavities therein which enable fluid access to the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, macrospheres or granules having a desired particle range, preferably from about 16 to about 60 mesh (Standard U.S. Mesh) (1.9 mm to 250 microns). Clays of the kaolin type, water permeable organic polymers or silica are generally used as binders.

Those skilled in the art will appreciate that the performance of an adsorbent is often greatly influenced by a number of factors not related to its composition such as operating conditions, feed stream composition and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For the subject process it is preferred that the water content of the adsorbent results in an LOI at 900° C. of less than 7.0% and preferably within the range of from 0 to 4.0 wt. %.

The silicalite active component of the adsorbent will ordinarily be in the form of small crystals present in the adsorbent particles in amounts ranging from about 75 to about 98 wt. % of the particle based on volatile-free composition. Volatile-free compositions are generally determined after the adsorbent has been calcined at 900° C in order to drive off all volatile matter. The remainder of the adsorbent will generally be the inorganic matrix of the binder present in intimate mixture with the small particles of the silicalite material. This matrix material may be an adjunct of the manufacturing process for the silicalite, for example, from the intentionally incomplete purification of the silicalite during its manufacture.

In the practice of the present invention, a feed mixture comprising one or more monomethyl branched hydrocarbon and at least one nonnormal hydrocarbon of like carbon number is passed through one or more beds of an adsorbent which selectively adsorbs the monomethyl branched hydrocarbon while permitting other components of the feed stream to pass through the adsorption zone in an unchanged condition. The feed may contain only paraffinic hydrocarbons or may be a mixture of paraffins and olefins such as the effluent of a dehydrogenation zone. The feed may also be a substantially pure stream of olefins having different molecular structures. The flow of the feed through the adsorbent bed is stopped and the adsorption zone is then flushed to remove nonadsorbed materials surrounding the adsorbent. Thereafter the desired isomer is desorbed from the adsorbent by passing a desorbent stream through the adsorbent bed. The desorbent material is commonly also used to flush nonadsorbed materials from the void spaces around and within the adsorbent.

The selectivity, ($\beta$), of an adsorbent/desorbent pair is defined as the ratio of the two components in the adsorbed phase divided by the ratio of the same two components in the unabsorbed phase at equilibrium conditions. Relative selectivity is given by the equation:

$$\text{Selectivity} = \text{wt. percent } C/\text{wt. percent } D_A/\text{wt. percent } C/\text{wt. percent } D_U$$

where C and D are two components of the feed represented in weight percent and the subscripts A and U represent the adsorbed and unabsorbed phases, respectively. The equilibrium conditions are determined when the feed passing over a bed of adsorbent does not change composition, in other words, when there is no net transfer of material occurring between the unabsorbed and adsorbed phases. Relative selectivity can be expressed not only for one feed compound as compared to another but can also be expressed between any feed mixture component and the desorbent material.

Where selectivity of two components approaches 1.0, there is no preferential adsorption of one component by the adsorbent with respect to the other; they are both adsorbed to about the same degree with respect to each other. As $\beta$ becomes less than or greater than 1.0, there is a preferential adsorption by the adsorbent for one component with respect to the other. When comparing the selectivity of the adsorbent for component C over component D, a $\beta$ larger than 1.0 indicates preferential adsorption of component C within the adsorbent. A $\beta$ less than 1.0 would indicate that component D is preferentially adsorbed leaving an unabsorbed phase richer in component C and an adsorbed phase richer in component D.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent.

Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and a temperature which insures liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

Feed mixtures which can be utilized in the process of this invention will typically be prepared by either prior separation step(s) or by relatively specific oligomerization or alkylation reactions. Such feed preparation methods are inherently imprecise and produce a stream containing a mixture of compounds. Thus, the feed mixtures to the process of this invention can contain sizable quantities of aromatic hydrocarbons and may also contain quantities of paraffins having multiple branches and paraffins having multiple carbon atoms in the branches, cycloparaffin, branched cycloparaffins or other compounds having boiling points relatively close to the desired compound isomer. It is expected that separation methods will provide a lower cost adequate feed and will therefore be the predominate feed source. The carbon number range of the monomethyl paraffins desired for the production of LAB is normally between 9 and 16, with 10 to 14 often being preferred. This range corresponds to linear paraffins boiling in the kerosene boiling point range, and kerosene fractions produced in petroleum refineries either by crude oil fractionation or by conversion processes therefore form suitable feed precursors. Fractions recovered from crude oil by fractionation will typically require hydrotreating for removal of sulfur and/or nitrogen prior to being fed to the subject process. The boiling point range of the kerosene fraction can be adjusted by prefractionation to adjust the carbon number range of the paraffins. In an extreme case the boiling point range can be limited such that only paraffins of a single carbon number predominate. Kerosene fractions contain a very large number of different hydrocarbons and the feed to the subject process can therefore contain 200 or more different compounds.

As normal paraffins are readily adsorbed by silicalite it is preferred the feed stream contain substantially no normal paraffins. That is the concentration of normal paraffins is preferably below 0.3 mol percent and more preferably below 0.2 mol percent. Such a feed stream is available as the raffinate stream of an adsorptive separation process which selectively recovers the normal paraffins in an extract stream. The raffinate stream from such a unit will be free of contaminants such as sulfur or nitrogen containing compounds, and will also have a suitably low concentration of normal paraffins. The use of such a raffinate stream as the feed to the subject separation process allows integration of the subject process into an existing LAB facility, with the two adsorptive separation steps being performed in series. The separately recovered normal paraffins and monomethyl paraffins can then be processed in a variety of ways. For instance each paraffin stream could be processed independently via dehydrogenation and aromatic alkylation to produce two separate LAB products. Each paraffin could be used to form a desired paraffin blend, or olefins derived from each paraffin could be admixed prior to alkylation.

Adsorption conditions in general include a temperature range of from about to about 250° C., with from about 60 to about 200° C. being more preferred. Temperatures from 90° C. to 160° C. are highly preferred. Adsorption conditions also preferably include a pressure sufficient to maintain the process fluids in liquid phase; which may be from about atmospheric to 600 psig. Desorption conditions generally include the same temperatures and pressure as used for adsorption conditions. Slightly different conditions may be preferred depending on the composition of the adsorbent and the feed.

A broad embodiment of the subject process may be characterized as a process for the adsorptive separation of a monomethyl paraffin from a feed mixture comprising the monomethyl paraffin and at least one other nonnormal paraffinic hydrocarbon, which process comprises contacting the feed mixture with a bed of an adsorbent comprising silicalite at adsorption promoting conditions and then removing adsorbed monomethyl paraffin from the adsorbent by contact with an desorbent compound comprising a $C_5$ or $C_6$ cycloparaffin and a $C_5$ or $C_6$ normal paraffinic hydrocarbon. A preferred embodiment of the subject process may be characterized as a process for the continuous simulated moving bed adsorptive separation of a desired monomethyl paraffin from a feed mixture comprising at least the desired monomethyl paraffin and a second compound, which process comprises passing a feed stream comprising said feed mixture through a first bed of an adsorbent comprising silicalite located in an adsorbent chamber which contains a number of compartmentalized beds of the adsorbent, which adsorbent selectively retains said monomethyl paraffin, with the adsorbent chamber containing multiple adsorbent beds being separated by transfer points for streams used in the process, and withdrawing a raffinate stream comprising the second compound from the adsorbent chamber; passing a desorbent stream comprising a naphthene or a $C_5$–$C_{10}$ normal paraffin into the adsorbent chamber, and removing an extract stream comprising the desorbent and the monomethyl paraffin from the adsorbent chamber; periodically incrementing the transfer points in the adsorbent chamber of the feed, desorbent, extract and raffinate streams to simulate countercurrent movement of the beds of adsorbent and the feed stream; and, recovering the monomethyl paraffin from the extract stream.

The preferred desorbents comprise a mixture of a normal paraffin and a cycloparaffin (naphthene). A mixture in which the normal and cycloparaffins have the same carbon number is highly preferred, with carbon numbers of the desorbent compounds being in the general range of 5 to 8. Preferred cycloparaffins are cyclopentane, cyclohexane and methyl cyclohexane. The preferred normal paraffin is n-hexane, and the desorbent may range from 0 to 100% normal paraffin. N-hexane is actually the strongest desorbent of these compounds, and a blend of normal and cyclo paraffins is often desired to adjust the strength of the desorbent. These blends may contain from about 10 to 90 vol. percent cycloparaffin, with the remainder being the normal paraffin. A desorbent blend containing 40 to 60 percent cycloparaffin is preferred. The desorbent may also be 100% cycloparaffin.

A "pulse test" procedure may be employed to test adsorbents with a particular feed mixture and desorbent material to measure such adsorbent characteristics as adsorptive capacity, selectivity, resolution and exchange rate. The basic pulse test apparatus consists of a tubular adsorbent chamber of approximately 70 cc volume having an inlet and outlet at opposite ends of the chamber. The chamber is contained within a temperature control means and pressure control equipment is used to maintain the chamber at a constant predetermined pressure. Quantitative and qualitative analytical equipment such as refractometers, polarimeters and chromatographs can be attached to an outlet line of the chamber and used to detect quantitatively and/or determine qualitatively one or more components in the effluent stream leaving the adsorbent chamber. During a pulse test, the adsorbent is first filled to equilibrium with a particular desorbent material by passing the desorbent material through the adsorbent chamber. A pulse of the feed mixture, sometimes diluted in desorbent, is then injected for a duration of one or more minutes. Desorbent flow is resumed, and the feed components are eluted as in a liquid-solid chromatographic operation. The effluent can be analyzed on-stream. Alternatively, or in addition effluent fractions can be collected and later analyzed separately. Traces of the envelopes of corresponding component peaks can then be plotted in terms of component concentration versus quantity of effluent. The large number of hydrocarbons in the feed stream of the subject tests makes this impractical.

From information derived from the pulse test the adsorbent/desorbent system performance can normally be rated in terms of retention volume for an extract or a raffinate component, selectivity for one component with respect to the other, stage time, the resolution between the components and the rate of desorption of an extract component by the desorbent. The retention volume of an extract or a raffinate component may be determined from the distance between the center of the peak envelope of an extract or a raffinate component and the peak envelope of a tracer component or some other known reference point. It is expressed in terms of the volume in cubic centimeters of desorbent pumped during the time interval corresponding to the distance between the peak envelopes.

The table below lists variables and results of small scale "pulse tests" performed to evaluate various desorbents and conditions on several feeds. The materials labeled Raffinate A and B are the raffinate streams of commercial adsorptive separation units which recover normal paraffins from a $C_{10}$–$C_{14}$ hydrocarbon fraction. The desorbent column indicates the volume percent of each component of the desorbent as specified by the footnotes.

| Run No. | Feed | Temp, ° C. | Desorbent * |
|---|---|---|---|
| 9577-77 | Raffinate A | 150 | 50 C5/50 N6 |
| 9577-85 | Raffinate A | 100 | 50 C5/50 N6 |
| 9937-01 | Raffinate A | 150 | 100 C6 |
| 9937-06 | Raffinate A | 150 | 70 C6/30 N6 |
| 9937-17 | Raffinate A | 150 | 50 C6/50 N6 |
| 9937-25 | Raffinate B | 150 | 50 C6/50 N6 |
| 9953-06 | Kerosene | 150 | 50 C6/50 N6 |

* C5 indicates cyclopentane
C6 indicates cyclohexane
N6 indicates n-hexane

An adsorbent comprising 80% silicalite and 20% silica binder was used in all tests. The tests were performed in a chromatographic column having an adsorbent volume of 9 g. The flow rate through the column was 1.21 cc/min.

The very large number of different compounds in the feed pulse, including several different monomethyl paraffins and the limitations inherent in the simple pulse test procedure results in the test results differing from those often reported with this test procedure for other separations. In these other separations, the feed may contain two to four components if specific isomers such as the xylenes are being separated. A plot of an analysis of the effluent of the pulse test will then often show slightly overlapping peaks for the different components. With the high number of compounds involved in the subject separation such resolution is not reasonably possible. The effectiveness of the separation was therefore determined by collecting fractions of the effluent and analyzing each fraction. A new fraction was taken every two minutes. The initial fractions had high concentrations of desorbent and were followed by fractions having high concentrations of the more highly branched nonnormal hydrocarbons. The desired monomethyl hydrocarbons tended to be concentrated in the fractions collected at the end of the pulse of feed components. The table below gives the concentration (wt percent) of monomethyl paraffins present in several different fractions of Run No. 9937-06.

| Fraction No. | MMP % |
|---|---|
| 18 | 34 |
| 19 | 48 |
| 20 | 60 |
| 22 | 55 |
| 24 | 60 |
| 26 | 77 |
| 28 | 77 |
| 32 | 79 |
| 38 | 96 |

For Run No. 9937-06, liquid collected as fractions No. 19 to 100 was combined. The combined liquid was analyzed and found to contain the following weight percentages of different structural classes of compounds on an adsorbent free basis.

| | |
|---|---|
| monomethyl branched | 64% |
| dimethyl branched | 2.7% |
| normal paraffins | 4.6% |

-continued

| | |
|---|---|
| aromatics | 4.1% |
| naphthenes | 13.9% |
| unknowns | 10.7% |

For Run No. 9937-17, liquid collected as fractions No. 23 to 50 was combined. The combined liquid was analyzed and found to contain the following weight percentages of different structural classes of compounds.

| | |
|---|---|
| monomethyl branched | 77% |
| dimethyl branched | 0.1% |
| normal paraffins | 9.6% |
| aromatics | 4.1% |
| naphthenes | 3.8% |
| unknowns | 4.8% |

A sample formed by combining liquid from fractions 23 to 48 of Run 9953-6 was analyzed and found to contain 67% monomethyl branched compounds and 9.3% normal paraffins.

In comparing this data to the performance which is normally desired in commercial separations it must be noted that the data is derived from screening tests used to compare the performance of different desorbent/adsorbent pairs or operating conditions. Better results in terms of selectivity will result from optimization in terms of adsorbent composition, desorbent composition and operating conditions. Further the use of simulated moving bed (SMB) technology or even better batch separation will improve the performance of the process.

What is claimed is:

1. A liquid-phase process for the adsorptive separation of a $C_9$ to $C_{16}$ monomethyl acyclic hydrocarbon from a feed mixture comprising the monomethyl acyclic hydrocarbon and at least one other acyclic hydrocarbon, which process comprises contacting the feed mixture with a bed of an adsorbent comprising silicalite at adsorption promoting conditions and then removing a selectively adsorbed monomethyl acyclic hydrocarbon from the adsorbent by contact with an unsubstituted $C_5$ or $C_6$ cycloparaffin.

2. The process of claim 1 wherein the process includes simulating the use of a moving bed of adsorbent.

3. The process of claim 1 wherein the bed of an adsorbent is part of a swing bed system in which a first chamber is being used in an adsorption step while a second chamber is being regenerated.

4. The process of claim 1 wherein the selectively adsorbed monomethyl acyclic hydrocarbon is a paraffin.

5. A liquid-phase process for the adsorptive separation of a $C_9$ to $C_{16}$ monomethyl paraffin from a feed mixture comprising the monomethyl paraffin and at least one other nonnormal paraffinic hydrocarbon, which process comprises contacting the feed mixture with a bed of an adsorbent comprising silicalite at adsorption promoting conditions and then removing adsorbed monomethyl paraffin from the adsorbent by contact with an desorbent compound comprising 40 to 60 vol. percent unsubstituted $C_5$ or $C_6$ cycloparaffin and a $C_5$ or $C_6$ normal paraffinic hydrocarbon.

6. A process for the continuous simulated moving bed adsorptive separation of a desired monomethyl paraffin from a $C_9$ to $C_{16}$ feed mixture comprising at least the desired monomethyl paraffin and a second compound, which process comprises:

a.) passing a liquid-phase feed stream comprising said $C_9$ to $C_{16}$ feed mixture through a first bed of an adsorbent comprising silicalite located in an adsorbent chamber, which adsorbent selectively retains said monomethyl paraffin, with the adsorbent chamber containing multiple adsorbent beds being separated by transfer points for streams used in the process, and withdrawing a raffinate stream comprising the second compound from the adsorbent chamber;

b.) passing a desorbent stream comprising a $C_5$–$C_8$ cycloparaffin and normal paraffin into the adsorbent chamber, and removing an extract stream comprising the desorbent and the monomethyl paraffin from the adsorbent chamber;

c.) periodically incrementing the transfer points in the adsorbent chamber of the feed, desorbent, extract and raffinate streams to simulate countercurrent movement of the beds of adsorbent and the feed stream; and, d.) recovering the monomethyl paraffin from the extract stream.

7. The process of claim 6 wherein the feed mixture comprises multibranched paraffins.

* * * * *